United States Patent
Räther et al.

(10) Patent No.: US 11,226,308 B2
(45) Date of Patent: Jan. 18, 2022

(54) DETERMINING THE REDUCED ION MOBILITY OF ION SPECIES BY TRAPPED ION MOBILITY SPECTROMETRY (TIMS)

(71) Applicant: Bruker Daltonik GmbH, Bremen (DE)

(72) Inventors: Oliver Räther, Lilienthal (DE); Karsten Michelmann, Bremen (DE)

(*) Notice: Subject to any disclaimer, the term of this patent is extended or adjusted under 35 U.S.C. 154(b) by 0 days.

(21) Appl. No.: 16/589,844

(22) Filed: Oct. 1, 2019

(65) Prior Publication Data

US 2020/0103373 A1 Apr. 2, 2020

(30) Foreign Application Priority Data

Oct. 1, 2018 (DE) .................. 102018124203-4

(51) Int. Cl.
  *G01N 27/622* (2021.01)
  *G16B 40/10* (2019.01)
  *G06F 17/18* (2006.01)

(52) U.S. Cl.
  CPC ........... *G01N 27/622* (2013.01); *G06F 17/18* (2013.01); *G16B 40/10* (2019.02)

(58) Field of Classification Search
  CPC .... G01N 27/622; G01N 27/624; G16B 40/10; G06F 17/18
  See application file for complete search history.

(56) References Cited

U.S. PATENT DOCUMENTS

| 6,630,662 B1 | 10/2003 | Loboda |
| 7,838,826 B1 | 11/2010 | Park |

FOREIGN PATENT DOCUMENTS

| EP | 3531122 A1 | 8/2019 |
| GB | 2490387 A | 10/2012 |
| GB | 2553398 A | 3/2018 |

OTHER PUBLICATIONS

Silveira, Joshua A., et al. "Fundamentals of trapped ion mobility spectrometry part II: fluid dynamics." Journal of the American Society for Mass Spectrometry 27.4 (2016): 585-595 (Year: 2016).*
Michelmann, Karsten, et al. "Fundamentals of trapped ion mobility spectrometry." Journal of the American Society for Mass Spectrometry 26.1 (2014): 14-24 (Year: 2014).*
Michelmann, Karasten et al., "Fundamentals of Trapped Ion Mobility Spectrometry", J. A,. Soc. Mass Spectrom. (2015) 26:14-24.
Bleiholder et al., "A Transferable, Sample-Independent Calibration Procedure for Trapped Ion Mobility Spectrometry (TIMS)", Anal. Chem., 2018, 90,9040-9047.

* cited by examiner

*Primary Examiner* — Wyatt A Stoffa
(74) *Attorney, Agent, or Firm* — Benoit & Côté Inc.

(57) ABSTRACT

The invention provides methods and devices for determining the reduced ion mobility $K_o$ of an ion species by trapped ion mobility spectrometry wherein the reduced ion mobility $K_o$ is determined from a measured arrival time $t_m$ of the ion species and predetermined instrumental parameters by applying the inverse of a system function: $K_o = SYS^{-1}(t_m, p_i)$ or from multiple arrival times $t_{m,i}$ of the ion species measured for multiple values of an instrumental parameter.

17 Claims, 8 Drawing Sheets

DETERMINING THE REDUCED ION MOBILITY OF ION SPECIES BY TRAPPED ION MOBILITY SPECTROMETRY (TIMS)

BACKGROUND OF THE INVENTION

Field of the Invention

The invention relates to methods and devices for determining reduced ion mobilities $K_o$ by trapped ion mobility spectrometry.

Description of the Related Art

Ion mobility spectrometry is an analytical technique which is used to investigate the mobility of analyte ions in a buffer gas. An inherent feature of ion mobility spectrometry is that the ion mobility depends on molecular geometries of the ions such that it is often possible to resolve and thus separate isomers or conformers that cannot be resolved by mass spectrometry.

The reduced ion mobility $K_o$ relates to the ion mobility K under the gas pressure P and gas temperature T:

$$K_o = K \frac{P}{P_o} \frac{T_o}{T}$$

where $T_o$ and $P_o$ are the standard temperature (273 K) and standard gas pressure (1013 hPa).

The reduced ion mobility $K_o$ can be converted into a momentum transfer cross section $\Omega$ (collisional cross section, CCS) via the Mason-Schamp equation:

$$K_o = \frac{3q}{16 n_o} \sqrt{\frac{2\pi}{\mu k_B}} \frac{1}{\Omega}$$

where q is the charge of the ion, T is the gas temperature, $n_o$ is the standard density of the buffer gas, $k_B$ is the Boltzmann constant, and $\mu$ is the reduced mass of the ion and the drift gas molecules. The reduced ion mobility $K_o$ and the collision cross section $\Omega$ are equivalent information and are often used interchangeably.

The accuracy of measured values of the reduced ion mobility (collisional cross section) takes on increased significance in a range of applications. For example, the reduced ion mobility which is measured by ion mobility spectrometry-mass spectrometry (IMS-MS) enables to elucidate structures of complex and dynamic biological systems. It is also used to identify metabolites in metabolomics studies and peptides in proteomics studies, in particular by coupling IMS-MS with liquid chromatography (LC).

In trapped ion mobility spectrometry (TIMS), ions are at first trapped along a non-uniform electric DC field (field gradient) by a counteracting gas flow or along a uniform electric DC field by a counteracting gas flow which has a non-uniform axial velocity profile (gas velocity gradient). The trapped ions are separated in space according to ion mobility and subsequently eluted (released) over time according to their mobility by adjusting one of the gas velocity and the electric DC field (U.S. Pat. No. 6,630,662 B1 by Loboda; U.S. Pat. No. 7,838,826 B1 by Park). A TIMS analyzer is commonly operated in the low pressure range of 2 to 500 Pa and uses an electric RF field for radially confining the ions. Regarding the theoretical basis of TIMS, see the article "Fundamentals of Trapped Ion Mobility Spectrometry" by Michelmann et al. (J. Am. Soc. Mass Spectrom., 2015, 26, 14-24).

Ion mobility calibration typically requires a calibration function and calibrants with known reduced ion mobility. An empirical calibration function used in TIMS is known from the article "High Resolution Trapped Ion Mobility Spectrometry of Peptides" by Silveira et al. (Anal. Chem., 2014, 86, 5624-5627):

$$K_o = a + \frac{b}{V_m}$$

where a and b are calibration constants and $V_m$ is approximately the voltage applied across the TIMS analyzer when the ion species is measured at the ion detector. The voltage $V_m$ can be derived from the measured arrival time of the ion species at the detector. The calibration constants are determined from fitting the known $K_o$ of the calibrants and the corresponding voltages $V_m$ of multiple calibrants.

Another calibration procedure is known from the article "A Transferable, Sample-Independent Calibration Procedure for Trapped Ion Mobility Spectrometry (TIMS)" by Bleiholder et al. (Anal. Chem., 2018, 90, 9040-9047).

The calibration strategy by Bleiholder et al. differs from the typical approach in three aspects. First, the calibration function is based on a solution to the Boltzmann transport equation but is not motivated by empirical observations. Second, they separate quantities that depend on the sample from those that depend on the instrument. Third, they perform a Taylor expansion for the instrument-dependent quantities and calibrate the Taylor expansion coefficients. The result is a calibration procedure for a trapped IMS instrument that is stated to be accurate, robust, and transferable.

SUMMARY OF THE INVENTION

In a first aspect, the invention provides a method for determining the reduced mobility $K_o$ of an ion species. The method comprises:
- providing ions of the ion species to a TIMS analyzer;
- trapping the ions in the TIMS analyzer by setting an electric DC field and gas flow of the TIMS analyzer;
- adjusting the strength of the electric DC field and/or the velocity of the gas flow in time to release the trapped ions of the ion species;
- measuring the arrival time $t_m$ of the released ions at an ion detector;
- determining instrumental parameters $p_i$ of the TIMS analyzer; and
- determining the reduced mobility $K_o$ by inverse of the system function: $K_o = SYS^{-1}(t_m, p_i)$.

The TIMS analyzer may comprise an electric DC field with a field gradient and a gas flow opposing the force of the electric DC field or a gas flow with a velocity gradient and an electric DC field opposing the drag force of the gas flow.

The arrival time $t_m$ of an ion species at the ion detector depends on the instrumental parameters and the reduced mobility to be determined: $t_m = SYS(K_o, p_i)$.

Preferably, the electric DC field of the TIMS analyzer comprises a field gradient and a plateau, which is located downstream of the field gradient and has a substantially constant electric DC field, and the gas flow has a substantially constant velocity at the beginning of the plateau. More preferably, the gas flow is directed downstream towards the ion detector and the electric DC field comprises a rising electric DC field gradient opposing the drag force of the gas flow.

The inverse of the system function SYS can be approximated by:

$$K_o = \frac{1}{\left(\frac{1}{2}\frac{\beta}{v_g}\sqrt{\frac{2L_p}{\beta}} + \sqrt{\left(\frac{1}{2}\frac{\beta}{v_g}\sqrt{\frac{2L_p}{\beta}}\right)^2 - \frac{\beta}{v_g}\left(t_m - t_t - \frac{E_0}{\beta}\right)}\right)^2} \frac{P}{P_o}\frac{T_o}{T}$$

wherein $t_m$ is the measured arrival time at the ion detector, $\beta$ is the scan speed, $v_g$ is the gas velocity at the plateau, $L_p$ is the effective length of the plateau, $E_o$ is the electrical field strength of the plateau at the start of the scan, $t_t$ is the transfer time between the end of the plateau and the ion detector (which can be zero if the detector is located directly at the end of the plateau), P is the gas pressure at the plateau and T is the gas temperature at the plateau. The electric DC field strength of the plateau $E_p(t)$ is preferably linearly decreased in time by the scan speed $\beta$:

$$E_p(t)=E_0-\beta t$$

In a second aspect, the invention provides a method for determining the reduced mobility $K_o$ of an ion species. The method comprises:
(a1) providing ions of the ion species to a TIMS analyzer;
(a2) trapping the ions in the TIMS analyzer by setting an electric DC field and gas flow of the TIMS analyzer;
(a3) adjusting the strength of the electric DC field and/or the velocity of the gas flow in time to release the trapped ions of the ion species;
(a4) measuring the arrival time $t_m$ of the released ions at an ion detector;
(b) repeating the steps (a1) to (a4) for at least two different values of an instrumental parameter x to obtain measured data $(t_m,x)_{i=1 \ldots n}$ wherein n is the number of measurements; and
(c) determining the reduced mobility $K_o$ by one of:
fitting a system function $t_m=SYS(x,p_i,K_o)$ to the measured data $(t_m,x)_{i=1 \ldots n}$ by varying the reduced mobility $K_o$; and
transforming the measured data $(t_m,x)_{i=1 \ldots n}$ determining polynomial coefficients $c_j$ by fitting a polynomial function to the transformed data $(\bar{t}_m,\bar{x})_{i=1 \ldots n}$ and determining the reduced mobility $K_o$ using the polynomial coefficients $c_j$ and inversed coefficient functions $C_j(K_o, p_i)$ of a transformed system function SYS:

$$\bar{t}_m = SYS(x, p_i, K_o) = \sum_{j=1}^{N} C_j(p_i, K_o)x^j$$

$$K_o = C_j^{-1}(p_i, c_j)$$

wherein $p_i$ are predetermined instrumental parameters which are not varied in the repeated measurements.

The TIMS analyzer may comprise an electric DC field with a field gradient and a gas flow opposing the force of the electric DC field or a gas flow with a velocity gradient and an electric DC field opposing the drag force of the gas flow.

Preferably, the electric DC field of the TIMS analyzer comprises a field gradient and a plateau, which is located downstream of the field gradient and has a substantially constant electric DC field, and the gas flow has a substantially constant velocity at the beginning of the plateau. More preferably, the gas flow is directed downstream towards the ion detector and the electric DC field comprises a rising electric DC field gradient opposing the drag force of the gas flow.

The system function $t_m=SYS(x,p_i,K_o)$ can be approximated by:

$$t_m(K_o, E_0, \beta, v_g, L_p, t_t) = \frac{E_0}{\beta} - \frac{v_g}{\beta}\frac{1}{K} + \sqrt{\frac{2L_p}{\beta}}\frac{1}{\sqrt{K}} + t_t \text{ with}$$

$$K = K_o \frac{P_o}{P}\frac{T}{T_o}$$

wherein $t_m$ is the arrival time at the ion detector, $\beta$ is the scan speed, $v_g$ is the gas velocity at the plateau, $L_p$ is the effective length of the plateau, $E_o$ is the electrical field strength of the plateau at the start of the scan, $t_t$ is the transfer time between the end of the plateau and the ion detector, K is the mobility, $K_o$ is the reduced mobility, P is the gas pressure at the plateau and T is the gas temperature at the plateau. The electric DC field strength of the plateau $E_p(t)$ is linearly decreased in time by the scan speed $\beta$: $E_p(t)=E_0-\beta t$. The varied instrumental parameter is preferably one of the length of the plateau $L_P$, the scan speed $\beta$ and the gas velocity $v_g$ at the plateau.

Each one of the instrumental parameters $p_i$ can be directly measured and/or determined from a parameter function $p_i=P_i(q_i)$ wherein $q_i$ (i=1 ... n, n≥1) is at least one measured instrumental parameter. The instrumental parameter $q_i$ can be one of the instrumental parameters $p_i$ or another instrumental parameter. Preferably, the gas pressure $P_{in}$ at the entrance and/or the gas pressure $P_{out}$ at the exit of the TIMS analyzer are measured and at least one of the instrumental parameters is determined by a parameter function depending on $P_{in}$, $P_{out}$ or both. More preferably, the gas velocity at the plateau $v_g$ and the gas pressure P at the plateau are determined by parameter functions which depend on $P_{in}$ and $P_{out}$. The gas temperature T at the plateau is preferably determined by a parameter function which depends on the gas temperature $T_{in}$ and the gas pressure $P_{in}$ measured at the entrance of the TIMS analyzer and optionally also on the gas pressure $P_{out}$ at the exit of the TIMS analyzer.

In all aspects of the invention, ions can be generated using one of spray ionization (e.g. electrospray ESI or thermal spray), desorption ionization (e.g. matrix-assisted laser/desorption ionization (MALDI) or secondary ionization), chemical ionization (API), photo-ionization (PI), electron impact ionization (EI), and gas-discharge ionization. The ionization can take place at or above atmospheric pressure or under vacuum (low, medium or high vacuum).

In all aspects of the invention, ions can be detected by one of a Faraday detector, a secondary electron multiplier (e.g. a microchannel plate) and an image-current detector. Furthermore, the ion detector is preferably a mass analyzer which can for example be one of a time-of-flight mass analyzer (in particular with orthogonal ion injection), an electrostatic ion trap, a RF ion trap, an ion cyclotron resonance analyzer and a quadrupole mass filter.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Figure 1A:
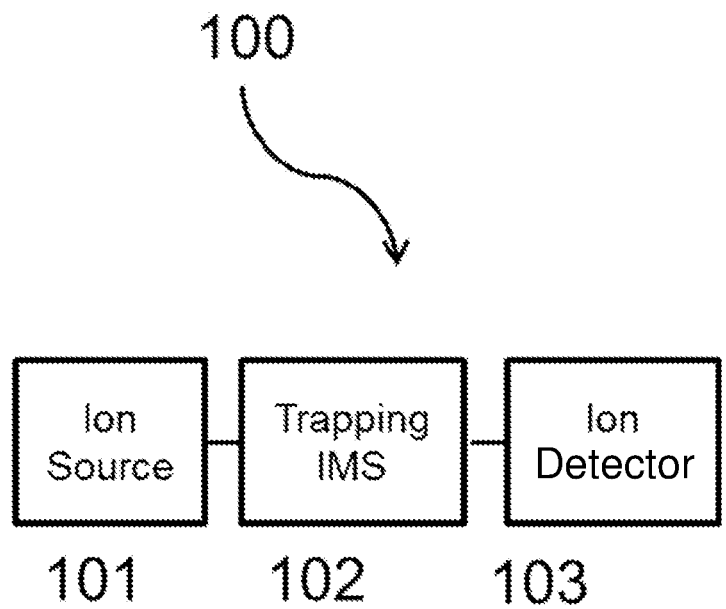
FIG. 1A shows a trapped ion mobility spectrometer (100) known in the art with a TIMS analyzer (102) which is coupled upstream to an ion source (101) and downstream to an ion detector (103).

FIG. 1A shows a trapped ion mobility spectrometer (100) known in the art with a TIMS analyzer (102) which is coupled to an ion source (101) and an ion detector (103). The methods according to the present invention can be performed on mobility spectra acquired with the trapped ion mobility spectrometer (100).

The ions can for example be generated using one of spray ionization (e.g. electrospray ESI or thermal spray), desorption ionization (e.g. matrix-assisted laser/desorption ionization (MALDI) or secondary ionization), chemical ionization (API), photo-ionization (PI), electron impact ionization (EI), and gas-discharge ionization. The ionization can take place at or above atmospheric pressure or under vacuum (low, medium or high vacuum).

The ions can for example be detected by one of a Faraday detector, a secondary electron multiplier (e.g. a microchannel plate) and an image-current detector.

Figure 1B:
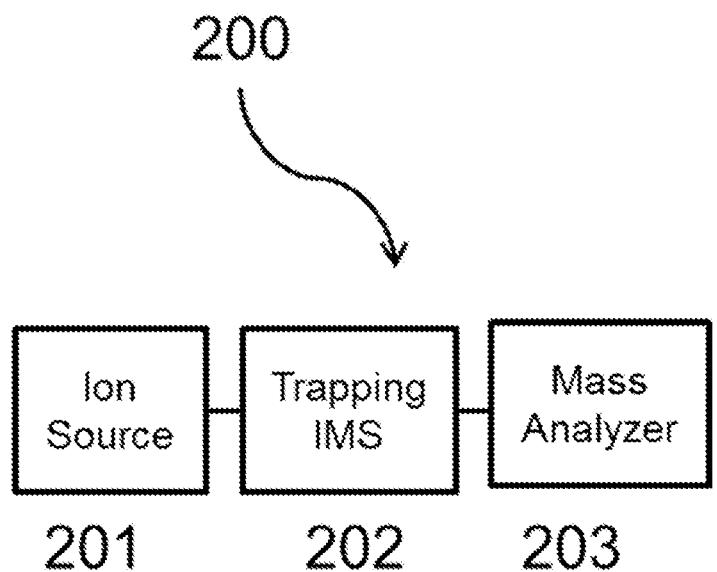
FIG. 1B shows a mass spectrometric system (200) known in the art with a TIMS analyzer (202) which is coupled upstream to an ion source (201) and downstream to a mass analyzer (203).

FIG. 1B shows a mass spectrometric system (200) known in the art with a TIMS analyzer (202) which is coupled to an ion source (201) and a mass analyzer (203).

The ions can for example be generated using one of spray ionization (e.g. electrospray ESI or thermal spray), desorption ionization (e.g. matrix-assisted laser/desorption ionization (MALDI) or secondary ionization), chemical ionization (API), photo-ionization (PI), electron impact ionization (EI), and gas-discharge ionization. The ionization can take place at or above atmospheric pressure or under vacuum (low, medium or high vacuum).

The mass analyzer can for example be one of a time-of-flight mass analyzer (e.g. with orthogonal ion injection), an electrostatic ion trap, a RF ion trap, an ion cyclotron resonance analyzer and a quadrupole mass filter. The mass spectrometric system (200) can additionally comprise one of a second TIMS analyzer, a mass filter (e.g. a quadrupole mass filter) and a fragmentation cell. The mass filter as well as the fragmentation cell can be located between the TIMS analyzer (202) and the mass analyzer (203) or between the ion source (201) and the TIMS analyzer (202).

Figure 2:
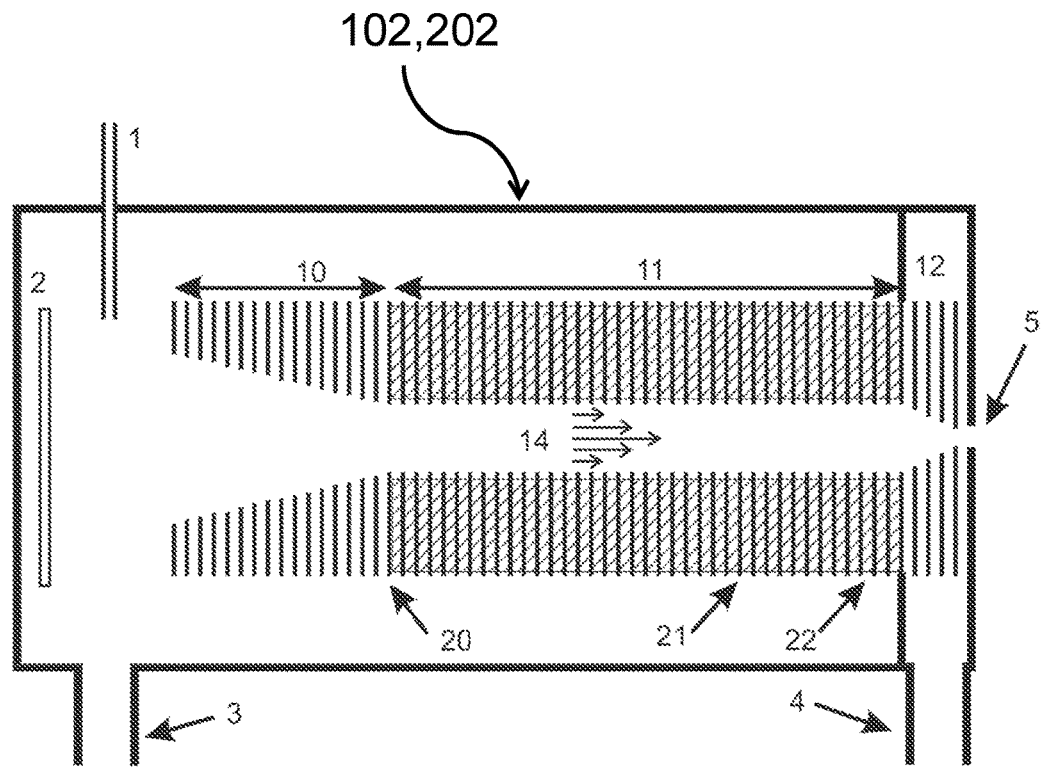
FIG. 2 shows a TIMS analyzer (102, 202) and a known operation thereof.

FIG. 2 shows a TIMS analyzer (102, 202) and a known operation of the TIMS analyzer (102, 202).

The TIMS analyzer (102, 202) is coupled to an electrospray ion source at atmospheric pressure (not shown). Entrained by gas from the ion source, ions are introduced via a transfer capillary (1) into the TIMS analyzer (102, 202).

A deflection plate (2) drives the ions into an entrance RF funnel (10) of the TIMS analyzer (102, 202). The entrance RF funnel (10) guides the ions into a TIMS tunnel (11) which comprises a stack of apertured electrodes. An exit RF funnel (12) is located downstream of the TIMS tunnel (11) for guiding ions through the outlet (5) towards an ion detector or mass analyzer (both not shown).

The pressure at the entrance and exit of the TIMS tunnel (11) is controlled by the pumping speed at ports (3) and (4). A pressure difference between the entrance and exit of the TIMS tunnel (11) generates a gas flow (14) inside the TIMS tunnel (11).

The electrodes of the TIMS tunnel (11) are typically segmented into quadrants, to allow for the generation of a radial quadrupolar electric RF field which confines ions near to the axis of the TIMS tunnel (11). Higher order RF fields can be generated by electrodes with more than four segments (e.g. six or eight segments).

The electrodes of the TIMS tunnel (11) are separated by an electrically insulating material closing the gaps between the electrodes around the tube which enables a well-defined gas flow (14) inside the TIMS tunnel (11). An electric DC field is generated inside the TIMS funnel (11) by applying electric DC potentials to the electrically isolated electrodes. The electric DC field forms an electric DC field barrier and comprises a rising electric DC field gradient (ramp) between electrode (20) and electrode (21) and a plateau between electrode (21) and (22).

The ions are guided through the entrance RF funnel (10) by an electric DC field and gas flow towards the entrance of the TIMS tunnel (11) and then pushed against the ramp of the electric DC field barrier by the gas flow (14).

Figure 2A:
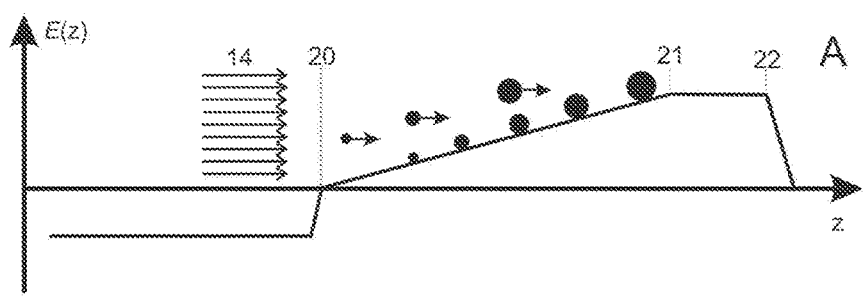
FIG. 2A shows schematically a first phase of operation of the analyzer of FIG. 2.
Figure 2B:
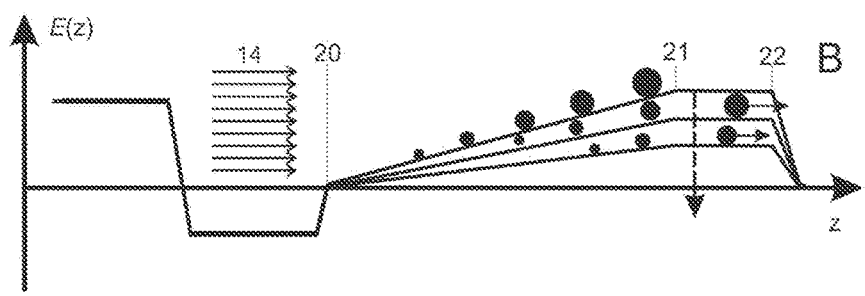
FIG. 2B shows schematically a second phase of operation of the analyzer of FIG. 2.

Two phases A and B of a typical operation of the TIMS analyzer (102, 202) are shown, respectively, in FIGS. 2A and 2B. The gas flow (14) inside the TIMS tunnel (11) is represented by arrows and drives the ions of different ion species against the ramp of the electric DC field barrier E(z). The different ion species are represented by dots of different size. The length of the gas flow arrows corresponds to the maximum velocity of the gas flow (14) on the axis of the TIMS tunnel (11) (z-axis).

In phase A ("accumulation phase"), ions are pushed by the gas flow (14) against the ramp of the electric DC field barrier E(z) and stopped there because they cannot surmount the electric DC field barrier E(z). The ions are accumulated at mobility dependent positions along the ramp of the electric DC field E(z) between the electrodes (20) and (21). Ions of low mobility (mainly heavy ions of large collision cross section) are collected in the high field near the upper end of the ramp, whereas ions of high mobility gather in the low field near the foot of the ramp, as indicated by the size of the dots symbolizing the size (or rather the CCS) of the ions of different ion species.

In phase B ("scan phase"), the electric DC voltage applied to the electrodes of the TIMS tunnel (11) is steadily decreased. Ions of increasing mobility are released successively in time towards an ion detector, particularly to a mass spectrometer. The arrival time $t_m$ of an ion species after starting the scan phase is a measure of the ion mobility of the ion species.

Figure 3:
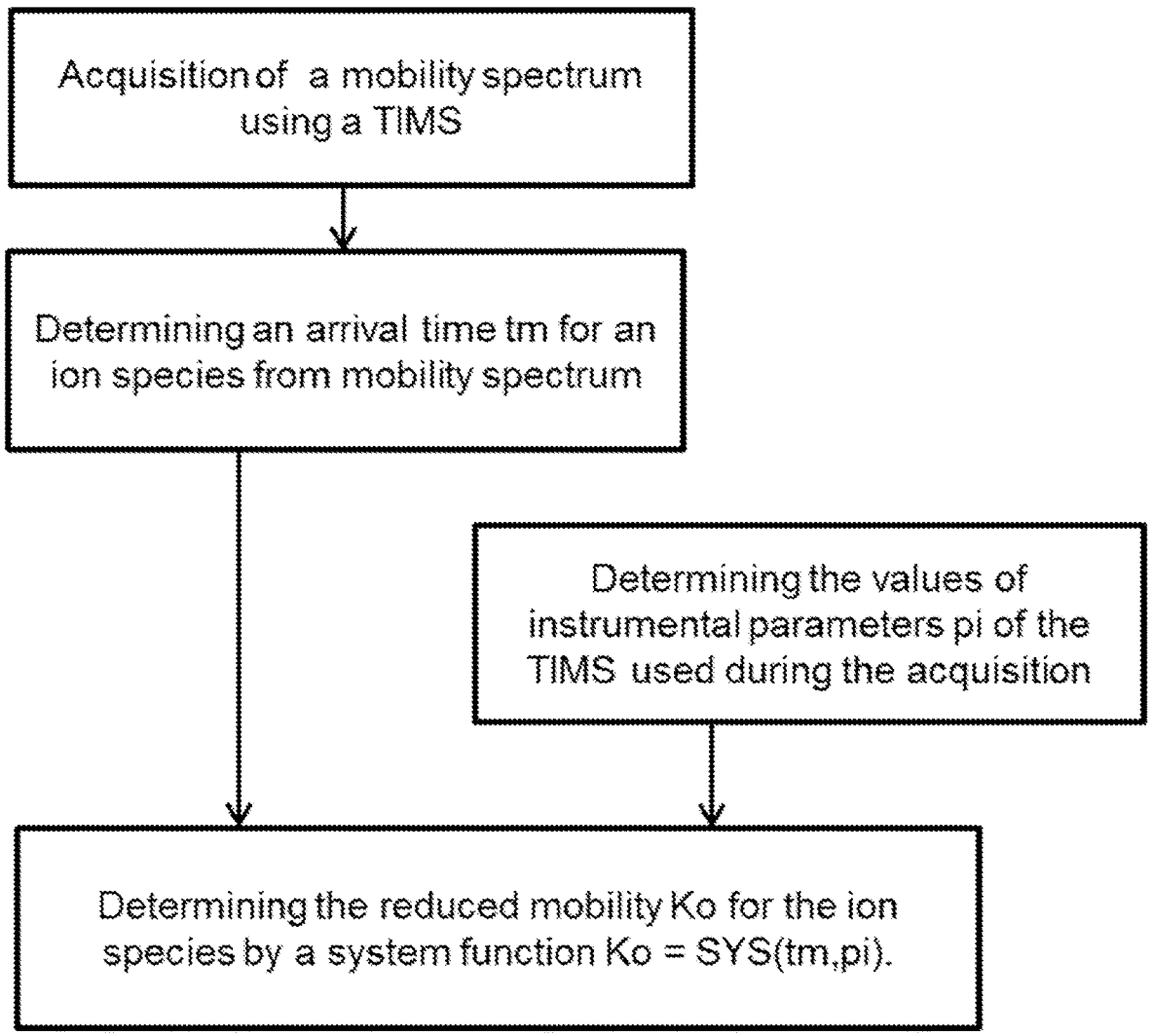
FIG. 3 is a flow chart showing a first exemplary method according to the invention.
Figure 4:
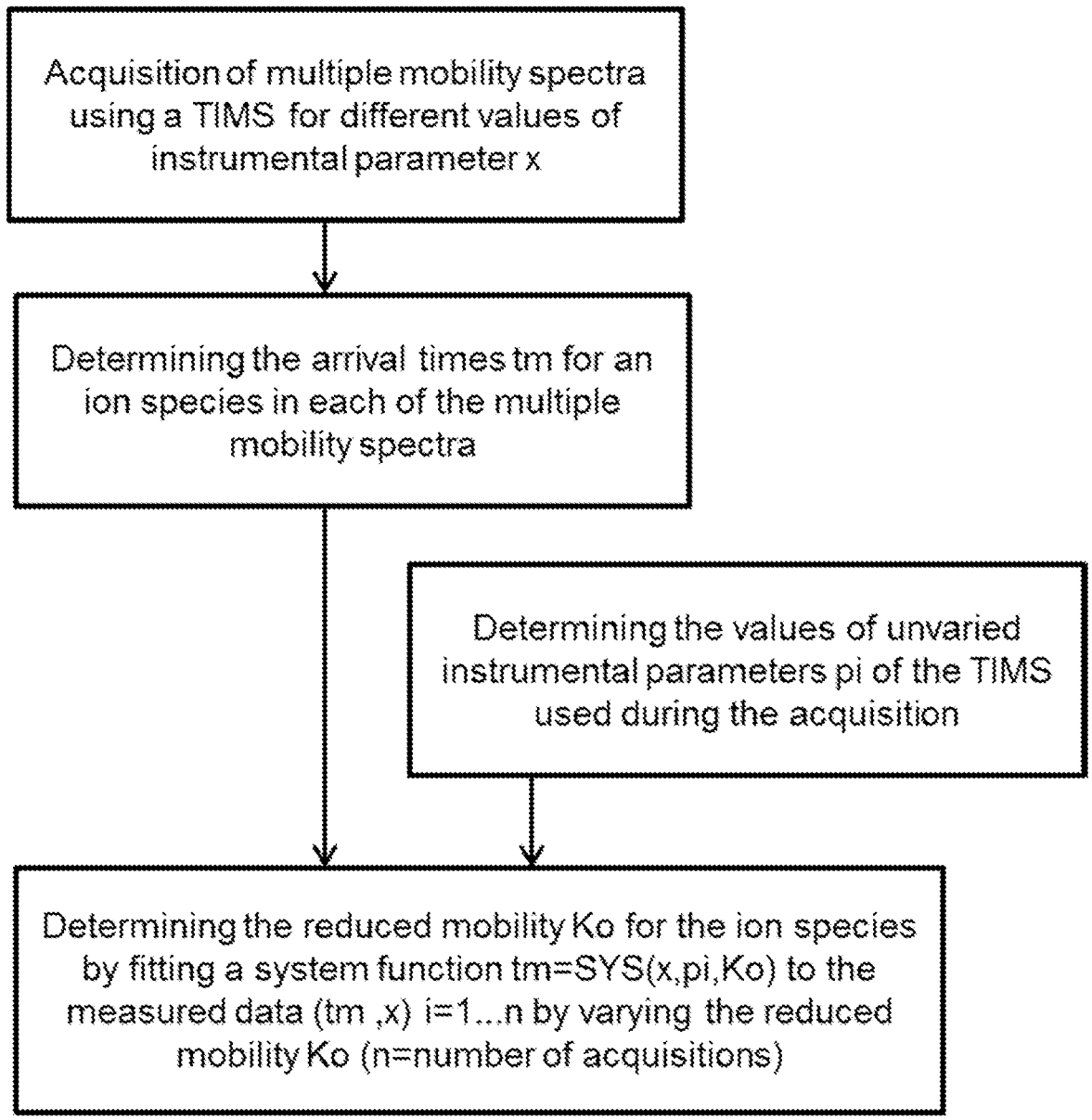
FIG. 4 is a flow chart showing a second exemplary method of the invention.
Figure 5:
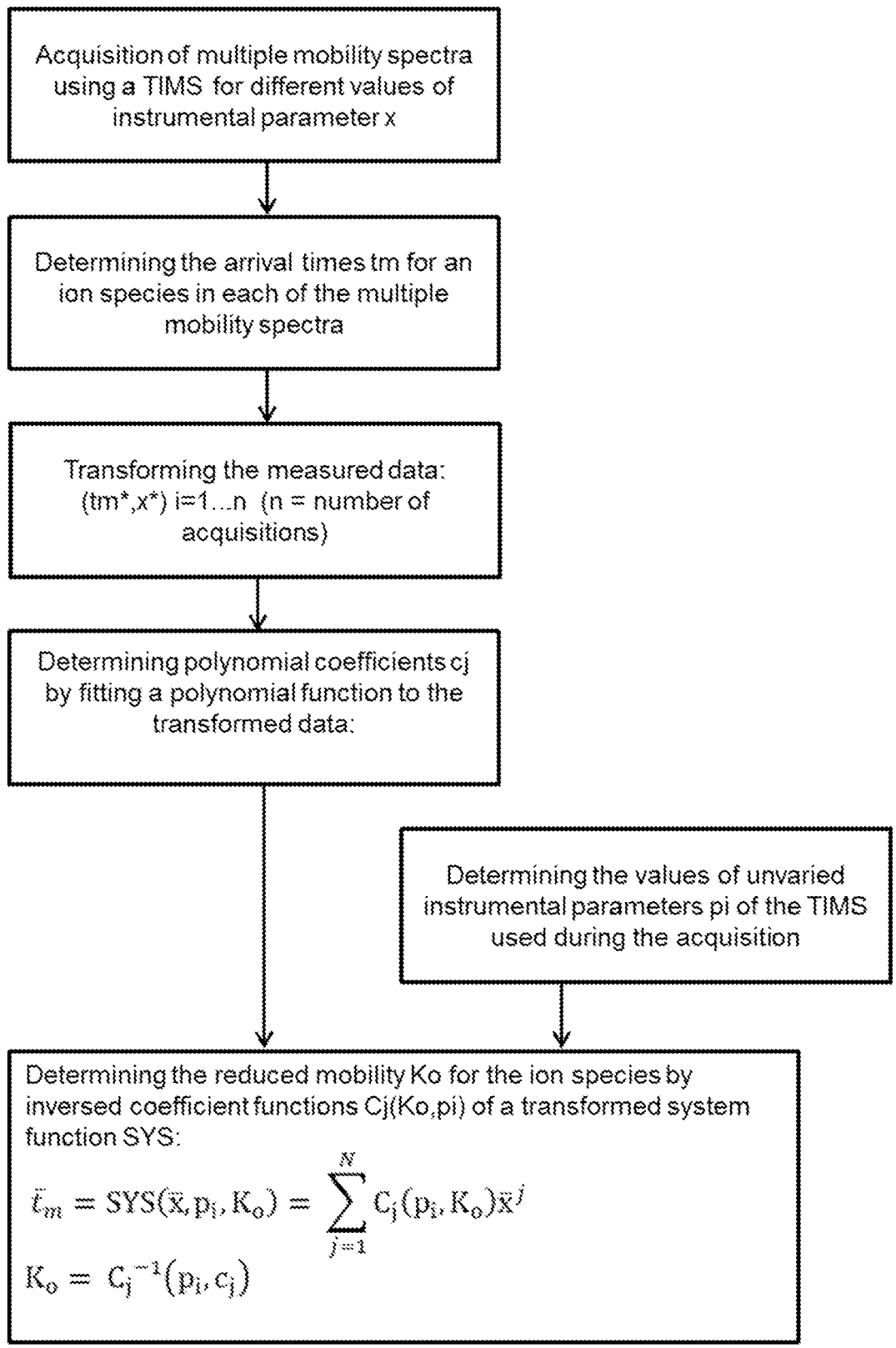
FIG. 5 is a flow chart showing a third exemplary method of the invention.

FIGS. 3, 4 and 5 show flow charts of the methods according to the invention.

In an exemplary embodiment, the height of the electric DC field barrier $E_p(t)$ of the TIMS analyzer (102, 202) is linearly decreased in time: $E_p(t)=E_0-\beta t$, wherein $E_o$ is the electric DC field at the plateau at the scan start $E_p(t=0)$ and $\beta$ is the scan speed.

The instrumental parameters $p_i$ of the TIMS analyzer (102, 202) comprise the scan speed $\beta$, the gas velocity at the plateau $v_g$, the effective length of the plateau $L_p$, the electrical field strength of the plateau at the start of the scan $E_o$, the transfer time $t_t$ between the end of the plateau and the downstream ion detector, the gas pressure at the plateau $P_{TIMS}$ and gas temperature at the plateau $T_{TIMS}$.

The system function $t_m=SYS(K_o,p_i)$ of the TIMS analyzer (102, 202) can then be approximated as follows:

$$t_m(K_o, E_o, \beta, v_g, L_p, t_t) = \frac{E_0}{\beta} - \frac{v_g}{\beta}\frac{1}{K} + \sqrt{\frac{2L_p}{\beta}}\frac{1}{\sqrt{K}} + t_t \text{ with}$$

$$K = K_o \frac{P_o}{P_{TIMS}} \frac{T_{TIMS}}{T_o}$$

wherein $t_m$ is the measured arrival time of an ion species at the ion detector, K is the mobility at gas pressure $P_{TIMS}$ and gas temperature $T_{TIMS}$, and $K_o$ is the reduced mobility.

The inverse of the system function $t_m=SYS(K_o,p_i)$ is given by:

$$K_o(t_m, E_o, \beta, v_g, L_p, t_t) =$$

$$\frac{2v_g^2}{L_p\beta}\left(1 + \sqrt{1 - \frac{2v_g}{L_p}\left(t_m - t_t - \frac{E_o}{\beta}\right)}\right)^{-2} \frac{P_{TIMS}}{P_o} \frac{T_o}{T_{TIMS}}$$

Now referring to FIG. 3, the reduced mobility $K_o$ is directly determined from the measured arrival time $t_m$ of an ion species and the instrumental parameters $p_i$, i.e. that merely a single measurement of the arrival time of the ion species is needed in the most basic embodiment. Of course, multiple measurements can be made for achieving a higher statistical confidence.

The scan speed $\beta$, the effective length of the plateau $L_p$ and the electrical field strength of the plateau $E_o$ are instrumental parameters which are related to the electric DC field barrier and can be directly derived from the electrode geometry of the TIMS tunnel (11) and the settings of the electric DC generator which supplies the electric DC potentials to the electrodes of the TIMS tunnel (11).

The gas velocity $v_g$, the gas pressure $P_{TIMS}$ and gas temperature $T_{TIMS}$ at the plateau are the instrumental parameters related to the gas flow (14). These instrumental parameters can be measured and/or determined by parameter functions wherein the parameter functions can depend on one or more other measured instrumental parameter.

Figure 7A:
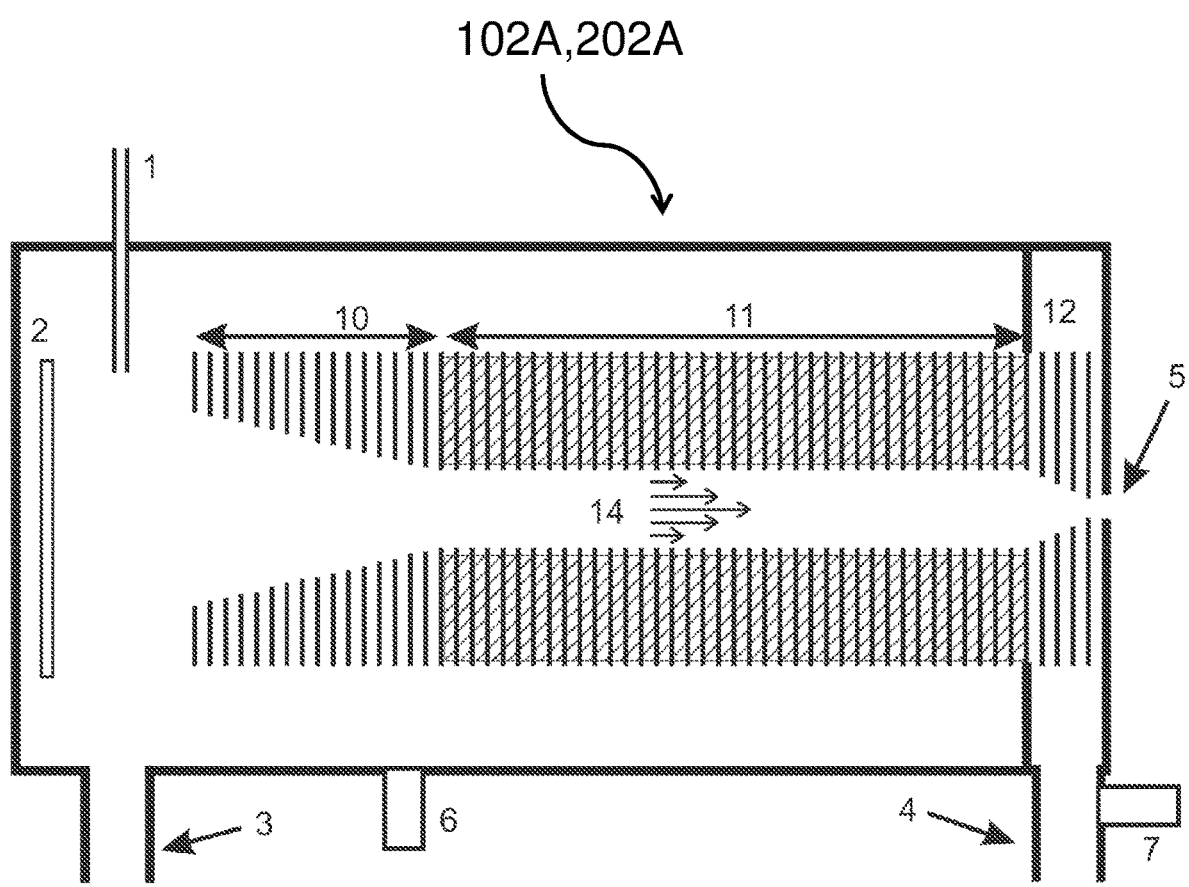
FIG. 7A shows a modified TIMS analyzer (102A, 202A) which comprises pressure gauges (6, 7) for measuring the gas pressure at the entrance $P_{in}$ and the $P_{out}$ of the TIMS analyzer (102A, 202A).

FIG. 7A shows a modified TIMS analyzer (102A, 202A) which comprises pressure gauges (6, 7) for measuring the gas pressure at the entrance $P_{in}$ and at the exit $P_{out}$ of the TIMS tunnel (11). The instrumental parameters of the gas flow (14) can for example be determined by parameter functions depending on the gas pressure at the entrance and exit of the TIMS tunnel (11) and on the gas temperature $T_{TIMS}$ at the entrance of the TIMS tunnel (11):

$$v_g = P_{vg}(P_{in}, P_{out}), P_{TIMS} = P_{PTIMS}(P_{in}, P_{out}), \text{ and}$$
$$T_{TIMS} = P_{TTIMS}(T_{in}, P_{in}, P_{out})$$

It is possible that instrumental parameters of the gas flow (14) can be determined with sufficient accuracy by a parameter functions which depend only on $P_{in}$ or $P_{out}$. In this case, measurement of one of these instrumental parameters is required.

Figure 7B:
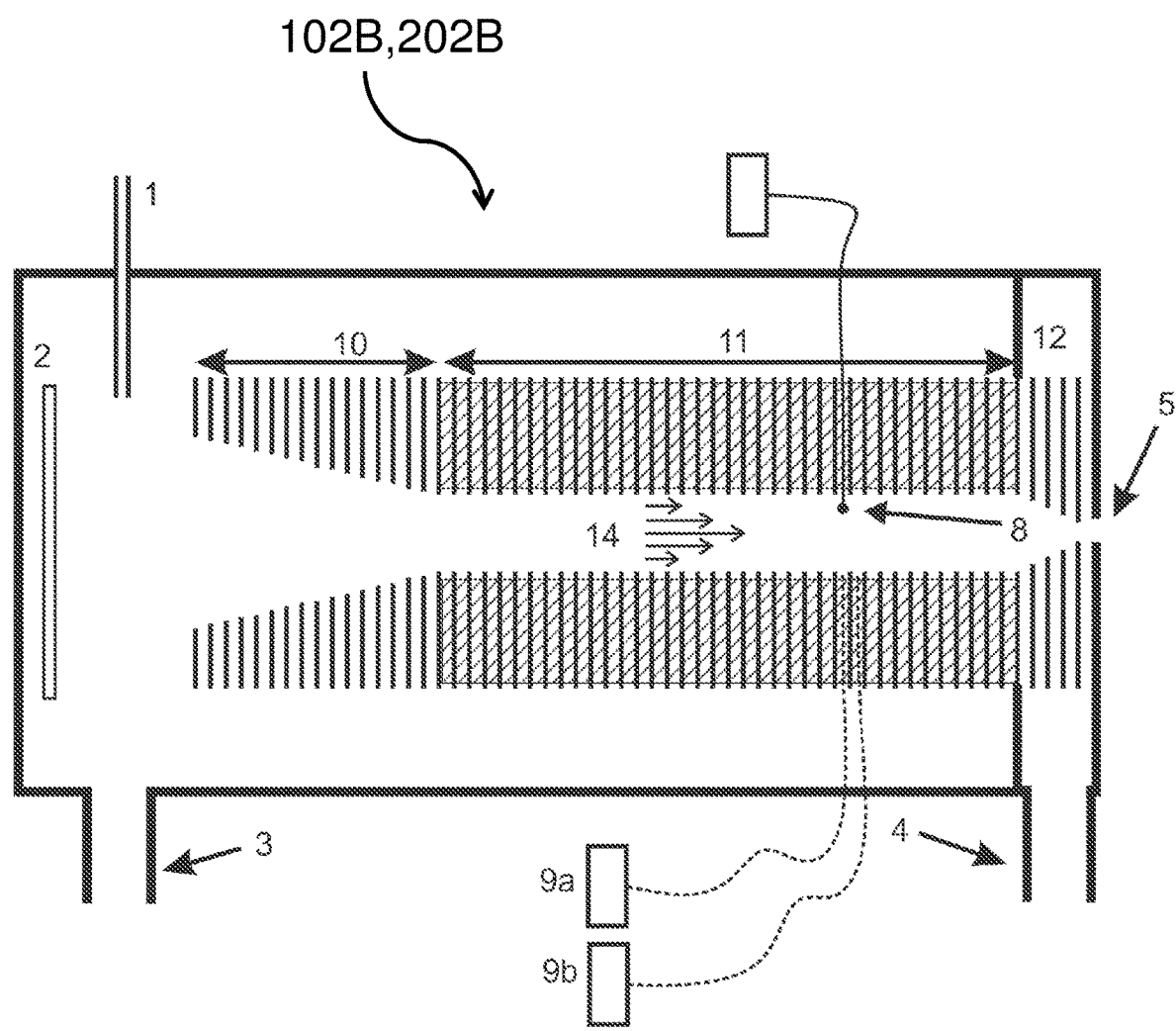
FIG. 7B shows a modified TIMS analyzer (102B, 202B) which comprises a sensor (8) for measuring the gas velocity $v_g$, a sensor (9a) for measuring the gas pressure $P_{TIMS}$, and a sensor (9b) for measuring the gas temperature $T_{TIMS}$ at the plateau of the TIMS analyzer (102B, 202B).

FIG. 7B shows a modified TIMS analyzer (102B, 202B) which comprises a sensor (8) for measuring the gas velocity $v_g$, a sensor (9a) for measuring the gas pressure $P_{TIMS}$, and a sensor (9b) for measuring the gas temperature $T_{TIMS}$ at the plateau of the TIMS analyzer (102B, 202B).

The velocity sensor (8) is preferably a hot wire anemometer. The hot wire can be shaped like a segment of a circle which is positioned symmetrically to the axis of the TIMS tunnel (11). The diameter is preferably less than 100 µm. The thickness and position of the hot wire are selected such that the wire substantially neither disturbs the gas flow (14) nor interacts with the ions which are confined near the axis by the electric RF field generated inside the TIMS tunnel (11).

The pressure sensor (9a) and temperature sensor (9b) are preferably optical fiber sensors which can be placed between the electrodes of the TIMS tunnel (11) and measure the local pressure and temperature of the gas at the plateau without disturbing the gas flow (14) and the electric DC field barrier. The gas pressure and temperature is preferably measured at the front end of the optical fiber.

It is further possible that a true subset of the instrumental parameters of the gas flow (14) is directly measured whereas the remaining instrumental parameters of the gas flow (14) are determined by parameter functions which depend on at least one instrumental parameter, like the gas pressure at the entrance $P_{in}$ and at the exit $P_{out}$ of the TIMS tunnel (11).

Now referring to FIG. 5, the system function $t_m=SYS(K_o, p_i)$ of the TIMS analyzer (102, 202) can then be approximated as follows:

$$t_m = \frac{E_0}{\beta} - \frac{v_g}{\beta}\frac{1}{K} + \sqrt{\frac{2L_p}{\beta}}\frac{1}{\sqrt{K}} + t_t \text{ with } K = K_o\frac{P_o}{P_{TIMS}}\frac{T_{TIMS}}{T_o}$$

The arrival time $t_m$ can be measured for different values of the scan speed $\beta$. Transforming the system function $t_m(\beta)$ by $1/\beta=x^2$ gives:

$$t_m(x) = E_0 x^2 - \frac{v_g}{K}x^2 + \sqrt{\frac{2L_p}{\beta}}x + t_t = \left(E_0 - \frac{v_g}{K}\right)x^2 + \sqrt{\frac{2L_p}{K}}x + t_t$$

Figure 6:
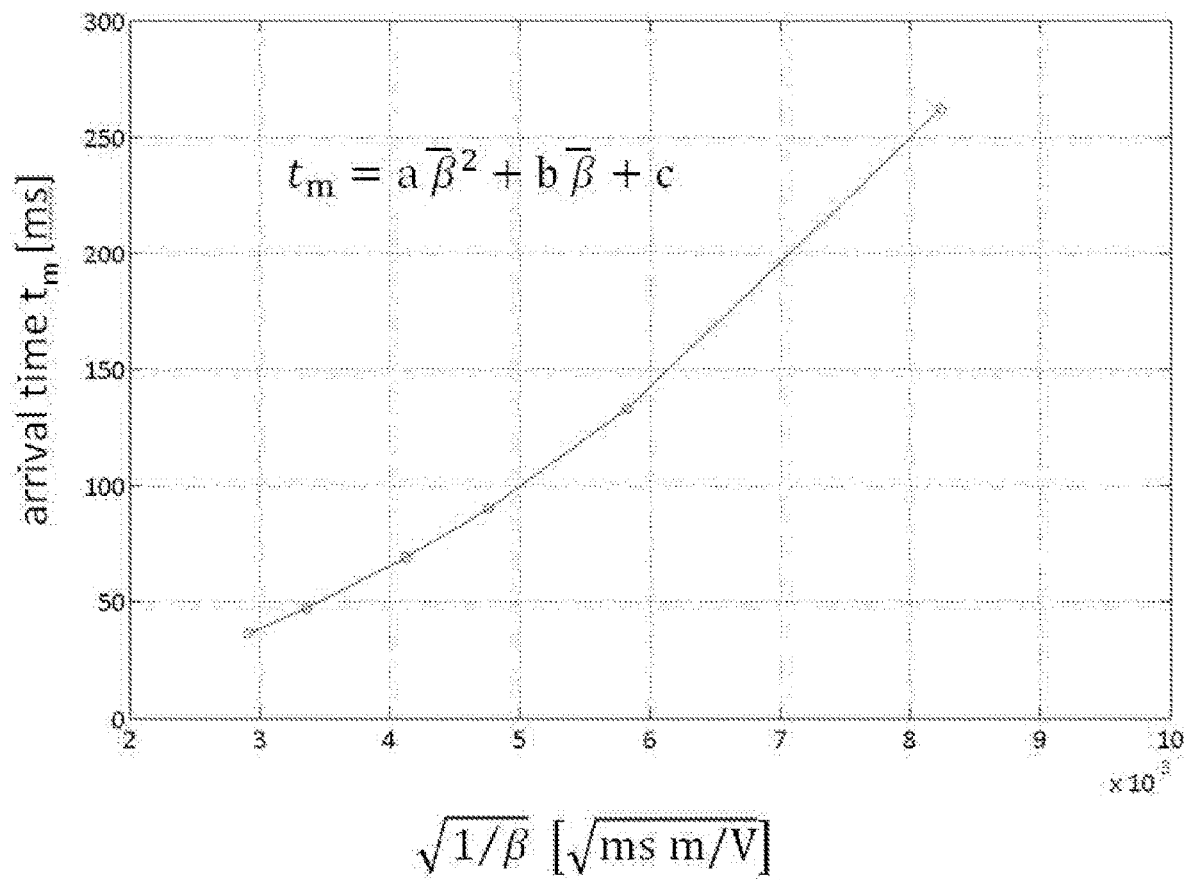
FIG. 6 shows an experimental result for one of the methods according to the invention.

The measured data $(t_m, x)$ are fitted by a polynomial of second order: $t_m(x)=ax^2+bx+c$. At least three different measurements are needed for a polynomial fit of second order. An example of second order fit to measured arrival times $t_m$ is shown in FIG. 6. The ion mobility K can be determined from the instrumental parameters $L_p$, $v_g$, $E_o$ and the polynomial coefficients a and b:

$$K = \frac{2L_p}{b^2}$$

$$K = -\frac{v_g}{a - E_0}$$

The arrival time $t_m$ can be measured for different values of the gas velocity $v_g$. Transforming the system function $t_m(v_g)$ by $v_g = x$ gives:

$$t_m(x) = -\frac{1}{\beta K}x + \left(\frac{E_0}{\beta} + \sqrt{\frac{2L_p}{\beta}}\frac{1}{\sqrt{K}} + t_t\right)$$

The measured data $(t_m,x)$ are fitted by a polynomial of first order: $t_m(x) = bx+c$. At least two different measurements are needed for the polynomial fit of first order. The ion mobility K can be determined from the instrumental parameters $\beta$ and the polynomial coefficients b:

$$K = -\frac{1}{\beta b}$$

The arrival time $t_m$ can be measured for different values of the length of the plateau $L_p$, for instance by short-cutting variable numbers of adjacent electrode plates at the end of the plateau. Transforming the system function $t_m(L_p)$ by $\sqrt{L_p}=x$ gives:

$$t_m(x) = \frac{E_0}{\beta} - \frac{v_g}{\beta}\frac{1}{K} + \sqrt{\frac{2}{K\beta}}x + t_t = \left(\frac{E_0}{\beta} - \frac{v_g}{\beta}\frac{1}{K} + t_t\right) + \sqrt{\frac{2}{K\beta}}x$$

The measured data $(t_m,x)$ are fitted by a polynomial of first order: $t_m(x) = bx+c$. At least two different measurements are needed for the polynomial fit of first order. The ion mobility K can be determined from the instrumental parameters $\beta$ and the polynomial coefficients b:

$$K = \frac{2}{\beta b^2}$$

The reduced mobility $K_o$ and thus collisional cross section can be determined from the ion mobility K and the gas pressure $P_{TIMS}$ and the gas temperature $T_{TIMS}$ at the plateau of the TIMS analyzer:

$$K = K_o \frac{P_o}{P_{TIMS}} \frac{T_{TIMS}}{T_o}$$

Like in the embodiments above, the instrumental parameters can be measured and/or determined by parameter functions wherein the parameter functions depend on one or more other measured instrumental parameter.

The gas velocity $v_g$, the gas pressure $P_{TIMS}$ and gas temperature $T_{TIMS}$ at the plateau are the instrumental parameters related to the gas flow. These instrumental parameters can be directly measured and/or determined by parameter functions wherein the parameter functions depend on one or more measured instrumental parameter, e.g. as described with reference to FIGS. 7A and 7B above.

The scan speed $\beta$, length of the plateau $L_p$ and the electrical field strength of the plateau $E_o$ are instrumental parameters which are related to the electric DC field barrier and can be directly derived from the electrode geometry of the TIMS tunnel (11) and the settings of the electric DC generator which supplies the electric DC potentials to the electrodes of the TIMS tunnel (11).

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method for determining the reduced mobility $K_o$ of an ion species by trapped ion mobility spectrometry (TIMS) comprising:

providing ions of the ion species to a TIMS analyzer which comprises an electric DC field with a field gradient and a gas flow opposing a force of the electric DC field or a gas flow with a velocity gradient and an electric DC field opposing a drag force of the gas flow;

trapping the ions in the TIMS analyzer by setting the electric DC field and the gas flow;

adjusting a strength of the electric DC field and/or a velocity of the gas flow in time to release the trapped ions;

measuring an arrival time $t_m$ of the released ions at an ion detector;

determining instrumental parameters $p_i$ of the TIMS analyzer; and determining the reduced mobility $K_o$ by inverse of a system function:

$K_o = SYS^{-1}(t_m, p_i)$, wherein the instrumental parameters comprise a gas velocity $v_q$ at a plateau of the electric DC field, a gas pressure P at the plateau and a gas temperature T at the plateau, wherein a gas pressure $P_{in}$ and a gas temperature $T_{in}$ at an entrance of the TIMS analyzer and a gas pressure $P_{out}$ at an exit of the TIMS analyzer are measured, wherein the gas velocity at the plateau $v_g$ and the gas pressure P at the plateau are determined by parameter functions which depend on $P_{in}$ and $P_{out}$, and wherein the gas temperature T at the plateau is determined by a parameter function which depends on $P_{in}$ and the gas temperature $T_{in}$.

2. The method according to claim 1, wherein the inverse of the system function SYS is approximated by:

$$K_o = \frac{1}{\left(\frac{1}{2}\frac{\beta}{v_g}\sqrt{\frac{2L_p}{\beta}} + \sqrt{\left(\frac{1}{2}\frac{\beta}{v_g}\sqrt{\frac{2L_p}{\beta}}\right)^2 - \frac{\beta}{v_g}\left(t_m - t_t - \frac{E_0}{\beta}\right)}\right)^2} \frac{P}{p_o}\frac{T_o}{T}$$

wherein $t_m$ is the measured arrival time at the ion detector, $\beta$ is a scan speed, $v_g$ is the gas velocity at the plateau, $L_p$ is an effective length of the plateau, $E_o$ is a strength of the electric DC field at the plateau at a start of a scan, $t_t$ is a transfer time between an end of the plateau and the ion detector, P is the gas pressure at the plateau, T is the gas temperature at the plateau, $T_o$ is a standard temperature and $P_o$ is a standard pressure.

3. The method according to claim 1, wherein the ion detector is one of a Faraday detector, a secondary electron multiplier, an image-current detector and a mass analyzer, said mass analyzer being one of time-of-flight with orthogonal ion injection, electrostatic ion trap, RF ion trap, ion cyclotron resonance analyzer and quadrupole mass filter.

4. The method according to claim 1, wherein the plateau is located downstream of the field gradient and has a substantially constant electric DC field, and the gas flow has a substantially constant velocity at a beginning of the plateau.

5. The method according to claim 4, wherein the gas flow is directed downstream towards the ion detector and the electric DC field comprises a rising electric DC field gradient opposing the drag force of the gas flow.

6. The method according to claim 5, wherein the electric DC field strength of the plateau $E_p$ is linearly decreased in time: $E_p(t)=E_0-\beta t$, wherein $E_o$ is the electrical field strength of the plateau at the start of the scan $E_p(t=0)$ and $\beta$ is the scan speed.

7. A method for determining the reduced mobility $K_o$ of an ion species by trapped ion mobility spectrometry (TIMS) comprising:
   (a1) providing ions of the ion species to a TIMS analyzer which comprises an electric DC field with a field gradient and a gas flow opposing a force of the electric DC field or a gas flow with a velocity gradient and an electric DC field opposing a drag force of the gas flow;
   (a2) trapping the ions in the TIMS analyzer by setting the electric DC field and the gas flow;
   (a3) adjusting a strength of the electric DC field and/or a velocity of the gas flow in time to release the trapped ions;
   (a4) measuring an arrival time $t_m$ of the released ions at an ion detector;
   (b) repeating the steps (a1) to (a4) for at least two different values of an instrumental parameter x to obtain measured data $(t_m,x)_{i=1 \ldots n}$ wherein n is the number of measurements; and
   (c) determining the reduced mobility $K_o$ by one of:
   fitting a system function $t_m=SYS(x,p_i,K_o)$ to the measured data $(t_m,x)_{i=1 \ldots n}$ by varying the reduced mobility $K_o$; and
   transforming measured data $(t_m,x)_{i=1 \ldots n}$, determining polynomial coefficients $c_j$ by fitting a polynomial function to the transformed data $(\bar{t}_m,\bar{x})_{i=1 \ldots n}$ and determining the reduced mobility $K_o$ using the polynomial coefficients $c_j$ and inversed coefficient functions $C_j(K_o,p_i)$ of a transformed system function SYS:

$$\bar{t}_m = SYS(x, p_i, K_o) = \sum_{j=1}^{N} C_j(p_i, K_o)x^j$$

$$K_o = C_j^{-1}(p_i,c_j)$$

wherein $p_i$ are predetermined instrumental parameters which are not varied in the repeated measurements.

8. The method according to claim 7, wherein the system function SYS is approximated by:

$$t_m(K_o, E_0, \beta, v_g, L_p, t_t) = \frac{E_0}{\beta} - \frac{v_g}{\beta}\frac{1}{K} + \sqrt{\frac{2L_p}{\beta}}\frac{1}{\sqrt{K}} + t_t \text{ with}$$

$$K = K_o \frac{P_o}{P}\frac{T}{T_o}$$

wherein $t_m$ is the arrival time at the ion detector, $\beta$ is a scan speed, $v_g$ is a gas velocity at a plateau of the electric DC field, $L_p$ is an effective length of the plateau, $E_o$ is a strength of the electric DC field at the plateau at a start of a scan, $t_t$ is a transfer time between an end of the plateau and the ion detector, K is the mobility, $K_o$ is the reduced mobility, P is a gas pressure at the plateau, T is a gas temperature at the plateau, $T_o$ is a standard temperature and $P_o$ is a standard pressure.

9. The method according to claim 7, wherein the instrumental parameter x is one of an effective length of a plateau $L_P$ of the electric DC field, a scan speed $\beta$ and a gas velocity $v_g$ at the plateau.

10. The method according to claim 8, wherein the varied instrumental parameter is one of the effective length of the plateau $L_P$, the scan speed $\beta$ and the gas velocity $v_g$ at the plateau.

11. The method according to claim 7, wherein each one of the instrumental parameters $p_i$ is measured and/or determined from a parameter function $p_i=P_i(q_i)$ wherein $q_i$ (i=1 . . . n, n≥1) is at least one measured instrumental parameter.

12. The method according to claim 7, wherein a gas pressure $P_{in}$ at an entrance and/or a gas pressure $P_{out}$ at an exit of the TIMS analyzer are measured and at least one of the instrumental parameters is determined by a parameter function of $P_{in}$, $P_{out}$ or both.

13. The method according to claim 12, wherein the instrumental parameters comprise a gas velocity $v_g$ at a plateau of the electric DC field, a gas pressure P at the plateau, and a gas temperature at the plateau, and wherein the gas velocity at the plateau $v_g$ and the gas pressure P at the plateau are determined by parameter functions which depend on $P_{in}$ and $P_{out}$ and wherein a gas temperature T at the plateau is determined by a parameter function which depends on $P_{in}$ and a gas temperature $T_{in}$ measured at the entrance of the TIMS analyzer.

14. The method according to claim 7, wherein the ion detector is one of a Faraday detector, a secondary electron multiplier, an image-current detector and a mass analyzer, said mass analyzer being one of time-of-flight with orthogonal ion injection, electrostatic ion trap, RF ion trap, ion cyclotron resonance analyzer and quadrupole mass filter.

15. The method according to claim 7, wherein the electric DC field comprises a field gradient and a plateau, which is located downstream of the field gradient and has a substantially constant electric DC field, and the gas flow has a substantially constant velocity at the beginning of the plateau.

16. The method according to claim 15, wherein the gas flow is directed downstream towards the ion detector and the electric DC field comprises a rising electric DC field gradient opposing the drag force of the gas flow.

17. The method according to claim 16, wherein the electric DC field strength of the plateau $E_p$ is linearly decreased in time: $E_p(t)=E_0 \beta t$, wherein $E_o$ is the electrical field strength of the plateau at the start of the scan $E_p(t=0)$ and $\beta$ is the scan speed.

\* \* \* \* \*